(12) United States Patent
Tanaka

(10) Patent No.: US 10,688,228 B2
(45) Date of Patent: Jun. 23, 2020

(54) SUCTION DEVICE

(71) Applicant: Murata Manufacturing Co., Ltd., Kyoto (JP)

(72) Inventor: Nobuhira Tanaka, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 147 days.

(21) Appl. No.: 15/451,722

(22) Filed: Mar. 7, 2017

(65) Prior Publication Data

US 2017/0173233 A1 Jun. 22, 2017

Related U.S. Application Data

(63) Continuation of application No. PCT/JP2015/073077, filed on Aug. 18, 2015.

(30) Foreign Application Priority Data

Sep. 9, 2014 (JP) ................. 2014-183548

(51) Int. Cl.
*A61M 1/06* (2006.01)
*A61M 1/00* (2006.01)
*A61M 39/22* (2006.01)
*A61M 39/26* (2006.01)

(52) U.S. Cl.
CPC ............ *A61M 1/06* (2013.01); *A61M 1/0035* (2014.02); *A61M 39/223* (2013.01); *A61M 2039/265* (2013.01); *A61M 2205/0294* (2013.01)

(58) Field of Classification Search
CPC ..... A61M 1/06; A61M 1/0035; A61M 39/223
See application file for complete search history.

(56) References Cited

U.S. PATENT DOCUMENTS 6,139,521 A 10/2000 Larsson
7,569,031 B2 * 8/2009 Britto ..................... A61M 1/06
604/315

(Continued)

FOREIGN PATENT DOCUMENTS

| JP | 2000-511443 A | 9/2000 |
| JP | 2013-533428 A | 8/2013 |
| WO | 2010/083485 A2 | 7/2010 |

OTHER PUBLICATIONS

International Search Report issued in Application No. PCT/JP2015/073077 dated Nov. 17, 2015.

(Continued)

*Primary Examiner* — Bradley J Osinski
(74) *Attorney, Agent, or Firm* — Pearne & Gordon LLP

(57) ABSTRACT

A breast pump (100) includes a left cup portion (1), a right cup portion (2), a tube (15, 16, 99), a pump (30), a container (14), a first switching valve (V1), a second switching valve (V1), and a control unit (70). The internal space of the tube (99) forms a passage (10). The passage (10) connects a first separator (S1) that communicates with a closed space (51), a second separator (S2) that communicates with a closed space (52), a discharge hole (31) of the pump (30), and a suction hole (32) of the pump (30). The first switching valve (V1) is provided within the tube (99) that is in the middle of the passage (10). The second switching valve (V2) is also provided within the tube (99) that is in the middle of the passage (10).

15 Claims, 18 Drawing Sheets

(56) References Cited

U.S. PATENT DOCUMENTS

| | | | | |
|---|---|---|---|---|
| 2005/0020971 | A1* | 1/2005 | McKendry | A61M 1/06 604/74 |
| 2005/0283112 | A1 | 12/2005 | Britto | |
| 2010/0324478 | A1* | 12/2010 | Kazazoglu | A61M 1/06 604/74 |
| 2011/0270163 | A1* | 11/2011 | Britto | A61M 1/06 604/74 |
| 2013/0123689 | A1* | 5/2013 | Bosman | A61M 1/1698 604/74 |

OTHER PUBLICATIONS

Written Opinion issued in Application No. PCT/JP2015/073077 dated Nov. 17, 2015.

* cited by examiner

SUCTION DEVICE

This is a continuation of International Application No. PCT/JP2015/073077 filed on Aug. 18, 2015 which claims priority from Japanese Patent Application No. 2014-183548 filed on Sep. 9, 2014. The contents of these applications are incorporated herein by reference in their entireties.

BACKGROUND OF THE DISCLOSURE

Field of the Disclosure

The present disclosure relates to a suction device that sucks a fluid.

Description of the Related Art

Hitherto, various suction devices that suck a fluid such as air have been devised. For example, Patent Document 1 discloses a breast pump 900 that is used by a mother or the like for taking the breast milk.

FIG. 16 is an external view showing the configuration of the breast pump 900 disclosed in Patent Document 1. FIG. 17 is an explanatory diagram showing the passage configuration of the breast pump 900 shown in FIG. 16. FIG. 18 is a diagram showing the change of the air pressure within a left cup portion 901 and the change of the air pressure within a right cup portion 902 while a pump 930 shown in FIG. 17 is operating.

As shown in FIG. 16, the breast pump 900 includes a suction drive unit 924 having the pump 930, the left cup portion 901 to be worn over the left breast, the right cup portion 902 to be worn over the right breast, and a tube 992. With this configuration, the breast pump 900 forms a passage 910 shown in FIG. 17. The pump 930 has a suction hole 932 and a discharge hole 931 for air.

The passage 910 has, between the suction hole 932 of the pump 930 and the left cup portion 901, a hole 918 connected to the outside of the passage 910 and a switching valve V91 for opening/closing the hole 918. The switching valve V91 further provides communication or causes a blockage between the suction hole 932 of the pump 930 and the left cup portion 901. Here, when a blockage is caused between the suction hole 932 and the left cup portion 901, the left cup portion 901 communicates with the outside of the passage 910.

In addition, the passage 910 has, between the suction hole 932 of the pump 930 and the right cup portion 902, a hole 919 connected to the outside of the passage 910 and a switching valve V92 for opening/closing the hole 919. The switching valve V92 further provides communication or causes a blockage between the suction hole 932 of the pump 930 and the right cup portion 902. Here, when a blockage is caused between the suction hole 932 and the right cup portion 902, the right cup portion 902 communicates with the outside of the passage 910.

In the above configuration, the switching valve V91 and the switching valve V92 alternately switch the passage 910 between a first form and a second form as shown in FIG. 17. The first form is a form in which the suction hole 932 and the left cup portion 901 communicate with each other and the suction hole 932 and the right cup portion 902 do not communicate with each other (i.e., the right cup portion 902 communicates with the outside of the passage 910). The second form is a form in which the suction hole 932 and the left cup portion 901 do not communicate with each other (i.e., the left cup portion 901 communicates with the outside of the passage 910) and the suction hole 932 and the right cup portion 902 communicate with each other.

With this configuration, the breast pump 900 is able to take breast milk from the left and right breasts with the single pump 930.

Patent Document 1: Japanese Unexamined Patent Application Publication (Translation of PCT Application) No. 2000-511443

BRIEF SUMMARY OF THE DISCLOSURE

However, the breast pump 900 of Patent Document 1 needs to suck breast milk, and thus requires a high suction flow rate. Therefore, the breast pump 900 needs to include a large-sized high-performance pump 930 in order to achieve a high suction flow rate.

Therefore, when an existing suction device including the breast pump 900 of Patent Document 1 achieves a high suction flow rate, the size thereof increases, and the manufacturing cost also increases.

An object of the present disclosure is to provide a suction device that is able to achieve a high suction flow rate with a small-sized low-cost pump.

A suction device according to the present disclosure includes: a pump having a discharge hole and a suction hole; a first worn portion having a first connection portion; a second worn portion having a second connection portion; a passage connecting the first connection portion, the second connection portion, the discharge hole, and the suction hole; and a switching mechanism provided in a middle of the passage and configured to switch the passage, wherein the switching mechanism switches the passage between: a first form in which the first connection portion and the suction hole communicate with each other, the second connection portion and the discharge hole communicate with each other, and the first connection portion and the second connection portion do not communicate with each other; and a second form in which the first connection portion and the discharge hole communicate with each other, the second connection portion and the suction hole communicate with each other, and the first connection portion and the second connection portion do not communicate with each other.

In this configuration, for example, the first worn portion and the second worn portion are worn over the left and right breasts. When the first worn portion is worn over the left breast, the first worn portion forms a first closed space between the breast and the first worn portion. The first closed space communicates with the first connection portion. When the second worn portion is worn over a right breast, the second worn portion forms a second closed space between the breast and the second worn portion. The second closed space communicates with the second connection portion.

In this configuration, by the switching mechanism switching the passage between the first form and the second form in a state where the pressure of the discharge hole of the pump is negative, the suction device is able to achieve a flow rate that is equal to or higher than a no-load flow rate of the pump.

Therefore, the suction device of the present disclosure is able to achieve a high suction flow rate with a small-sized low-cost pump.

In addition, the switching mechanism preferably alternately switches the passage between the first form and the second form.

Moreover, the switching mechanism preferably switches the passage to a third form in which the first connection portion and the second connection portion communicate with each other, both the first connection portion and the second connection portion communicate with the suction hole, and both the first connection portion and the second connection portion do not communicate with the discharge hole.

In this configuration, since it is possible to stop the operation of the pump during the third form, it is possible to reduce the power consumption.

The passage preferably has, between the discharge hole and the switching mechanism in the passage, an air vent connected to an outside of the passage and a vent valve configured to open/close the air vent.

In this configuration, since the vent valve is opened to cause the air pressure within the passage to be the atmospheric pressure when the suction device is not used, the load on the passage, the first worn portion, and the second worn portion is low.

In addition, since it is possible to detach the first worn portion and the second worn portion after the vent valve is opened to return the air pressure within the passage to the atmospheric pressure, the load on the human body is low.

The switching mechanism preferably includes a valve. The valve is more preferably a solenoid valve. The solenoid valve is more preferably a three-port solenoid valve.

In addition, preferably, the pump includes a piezoelectric element and is operated by the piezoelectric element.

In this configuration, since the pump uses, as a drive source, the piezoelectric element which generates small noise and vibration when operating, it is possible to reduce the noise of the suction device.

According to the present disclosure, it is possible to achieve a high suction flow rate with a small-sized low-cost pump.

DETAILED DESCRIPTION OF THE DISCLOSURE

Hereinafter, a breast pump 100 according to a first embodiment of the present disclosure will be described.

Figure 1:
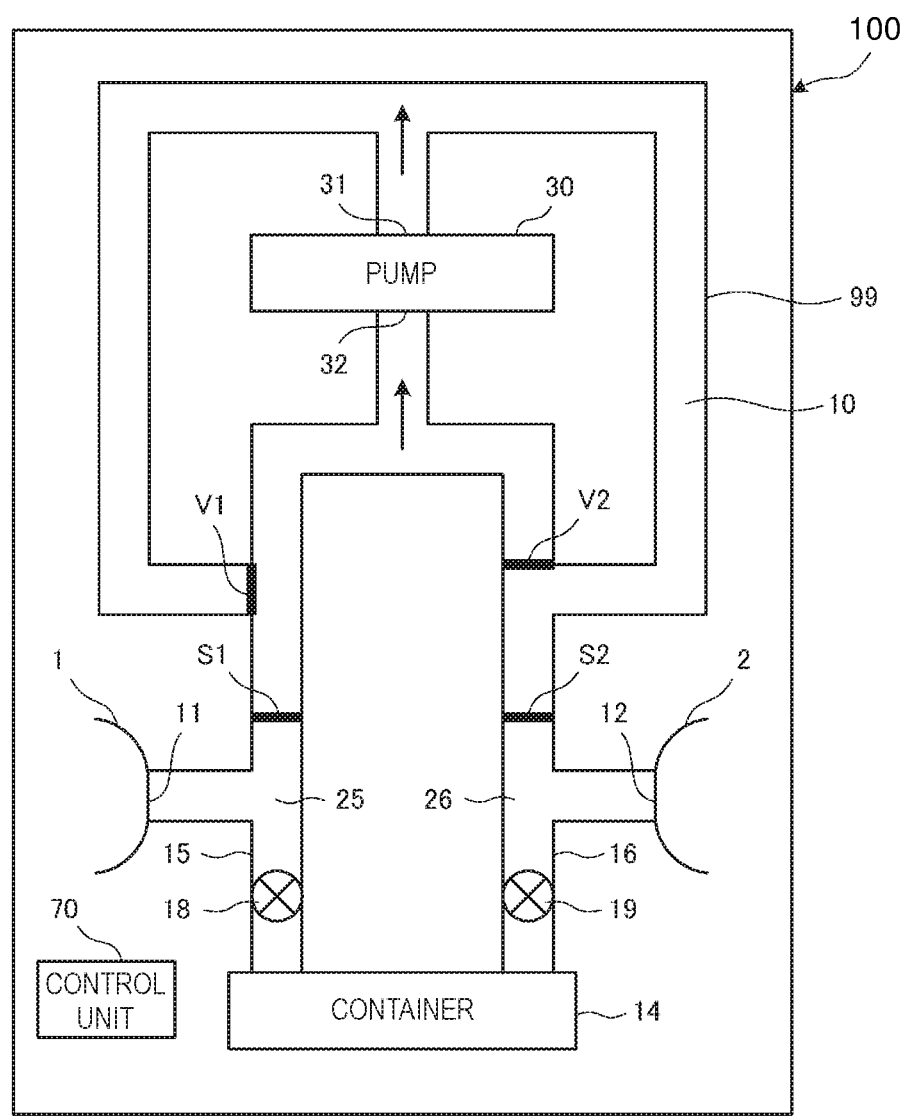
FIG. 1 is an explanatory diagram showing the configuration (a first form) of a breast pump 100 according to a first embodiment of the present disclosure.
Figure 2:
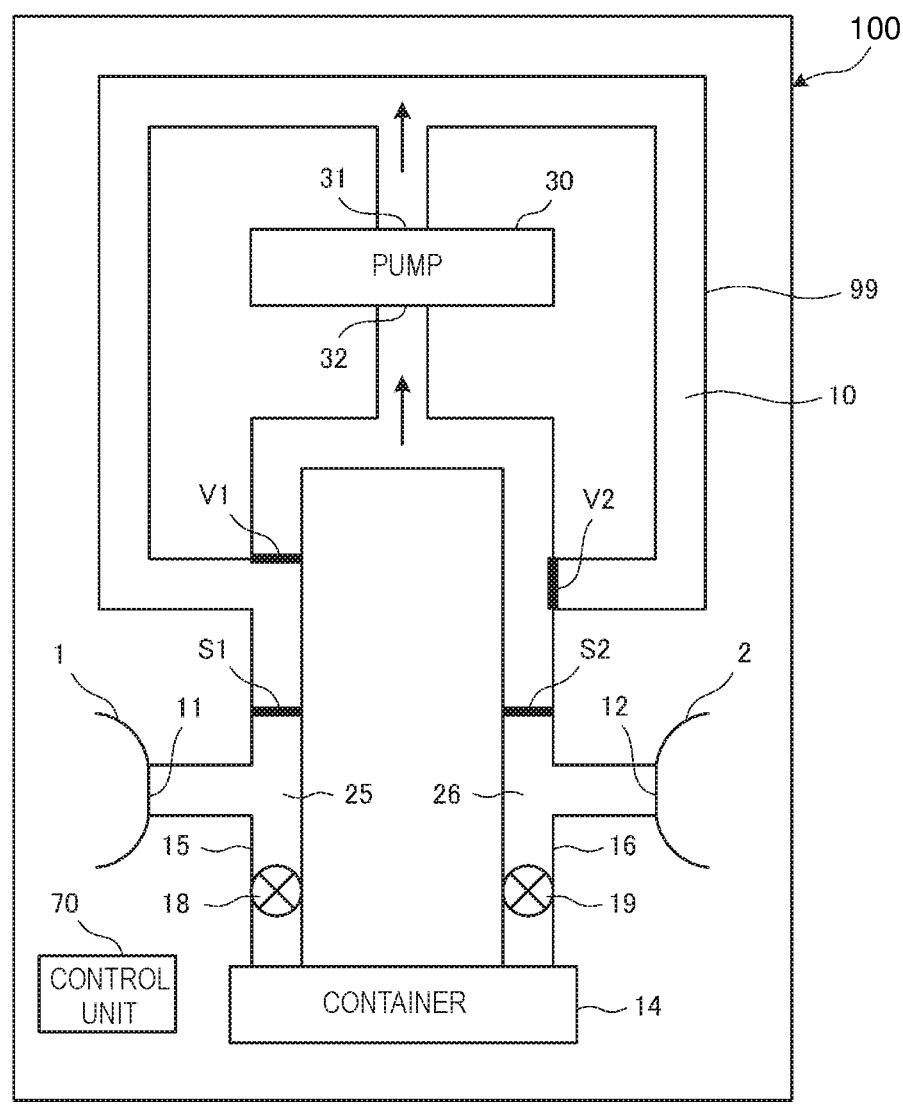
FIG. 2 is an explanatory diagram showing a configuration when a passage 10 is switched to a second form in the breast pump 100 shown in FIG. 1.
Figure 3:
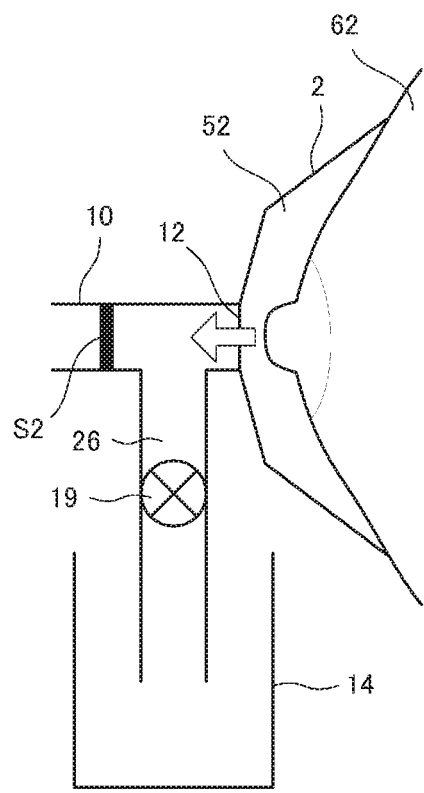
FIG. 3 is an explanatory diagram showing a state when a left cup portion 1 and a right cup portion 2 in the breast pump 100 shown in FIG. 1 are worn over the left and right breasts.
Figure 3:
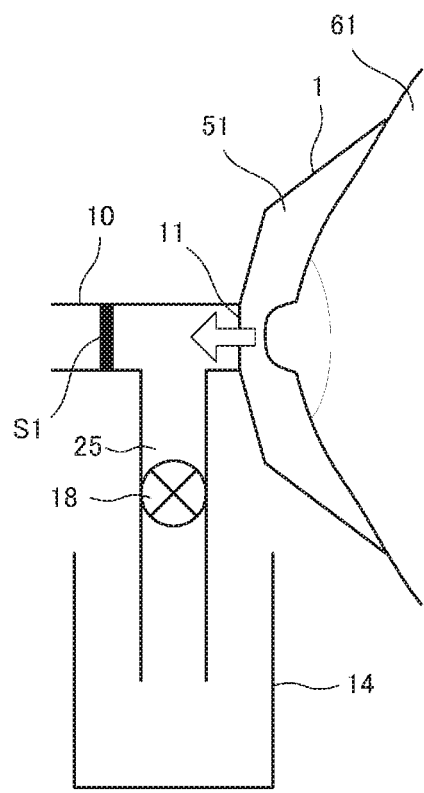

FIG. 1 is an explanatory diagram showing the configuration (the first form) of the breast pump 100 according to the first embodiment of the present disclosure. FIG. 2 is an explanatory diagram showing a configuration when a passage 10 is switched to the second form in the breast pump 100 shown in FIG. 1. FIG. 3 is an explanatory diagram showing a state when a left cup portion 1 and a right cup portion 2 in the breast pump 100 shown in FIG. 1 are worn over the left and right breasts.

The arrows shown in FIGS. 1 and 2 indicate the flow of the air. The arrows shown in FIG. 3 indicate flow of breast milk.

The breast pump 100 includes the left cup portion 1, the right cup portion 2, tubes 15, 16, and 99, a pump 30, a container 14, a first switching valve V1, a second switching valve V2, and a control unit 70.

The left cup portion 1 and the tube 15 correspond to a first worn portion of the present disclosure. In addition, the right cup portion 2 and the tube 16 correspond to a second worn portion of the present disclosure. Moreover, the first switching valve V1 and the second switching valve V2 form a switching mechanism of the present disclosure.

The left cup portion 1 is used to be worn over the left breast 61. The left cup portion 1 has a first passage port 11 connected to the tube 15. When the left cup portion 1 is worn over the left breast 61, the left cup portion 1 forms a closed space 51 between the left breast 61 and the left cup portion 1.

The internal space of the tube 15 forms a left passage 25 that communicates with the closed space 51 via the passage port 11. A first separator S1 that separates the passage 10 at the pump 30 side and the left passage 25 at the container 14 side is provided at the boundary between the tubes 99 and 15. The tubes 99 and 15 are connected to each other at the location where the first separator S1 is provided. The first separator S1 is composed of a film-like elastic body such as a rubber film. The first separator S1 is disposed such that the principal surfaces thereof are parallel to a cross-section of the tube 15.

Similarly, the right cup portion 2 is used to be worn over the right breast 62. The right cup portion 2 has a second passage port 12 connected to the tube 16. When the right cup portion 2 is worn over the right breast 62, the right cup portion 2 forms a closed space 52 between the right breast 62 and the right cup portion 2.

The internal space of the tube 16 forms a right passage 26 that communicates with the closed space 52 via the passage port 12. A second separator S2 that separates the passage 10 at the pump 30 side and the right passage 26 at the container 14 side is provided at the boundary between the tubes 99 and 16. The tubes 99 and 16 are connected to each other at the location where the second separator S2 is provided. The second separator S2 is composed of a film-like elastic body such as a rubber film. The second separator S2 is disposed such that principal surfaces thereof are parallel to a cross-section of the tube 16.

The first separator S1 corresponds to a first connection portion of the present disclosure. In addition, the second separator S2 corresponds to a second connection portion of the present disclosure.

The container 14 stores the breast milk coming out from the left breast 61 or the right breast 62. The container 14 is connected to the left cup portion 1 via the tube 15 and connected to the right cup portion 2 via the tube 16. Thus, the internal space of the container 14 communicates with the closed spaces 51 and 52 via the left passages 25 and 26, respectively.

A check valve 18 that prevents a fluid from flowing back from the container 14 to the left passage 25 is preferably provided in the tube 15. In addition, a check valve 19 that prevents a fluid from flowing back from the container 14 to the right passage 26 is preferably provided in the tube 16.

The pump 30 includes a piezoelectric element and is operated by the piezoelectric element. The pump 30 has a discharge hole 31 through which air is discharged, and a suction hole 32 through which air is sucked. The suction hole 32 and the discharge hole 31 of the pump 30 are connected to the tube 99.

The internal space of the tube 99 forms the passage 10. The passage 10 connects the first separator S1, the second separator S2, the discharge hole 31 of the pump 30, and the suction hole 32 of the pump 30.

The materials of the tubes 15, 16, and 99 are, for example, polypropylene or polyethylene.

The first switching valve V1 is provided within the tube 99 that is in the middle of the passage 10. The second switching valve V2 is also provided within the tube 99 that is in the middle of the passage 10.

The control unit 70 controls the opening/closing of the first switching valve V1 and the second switching valve V2. The control unit 70 is composed of, for example, a microcomputer.

Figure 4:
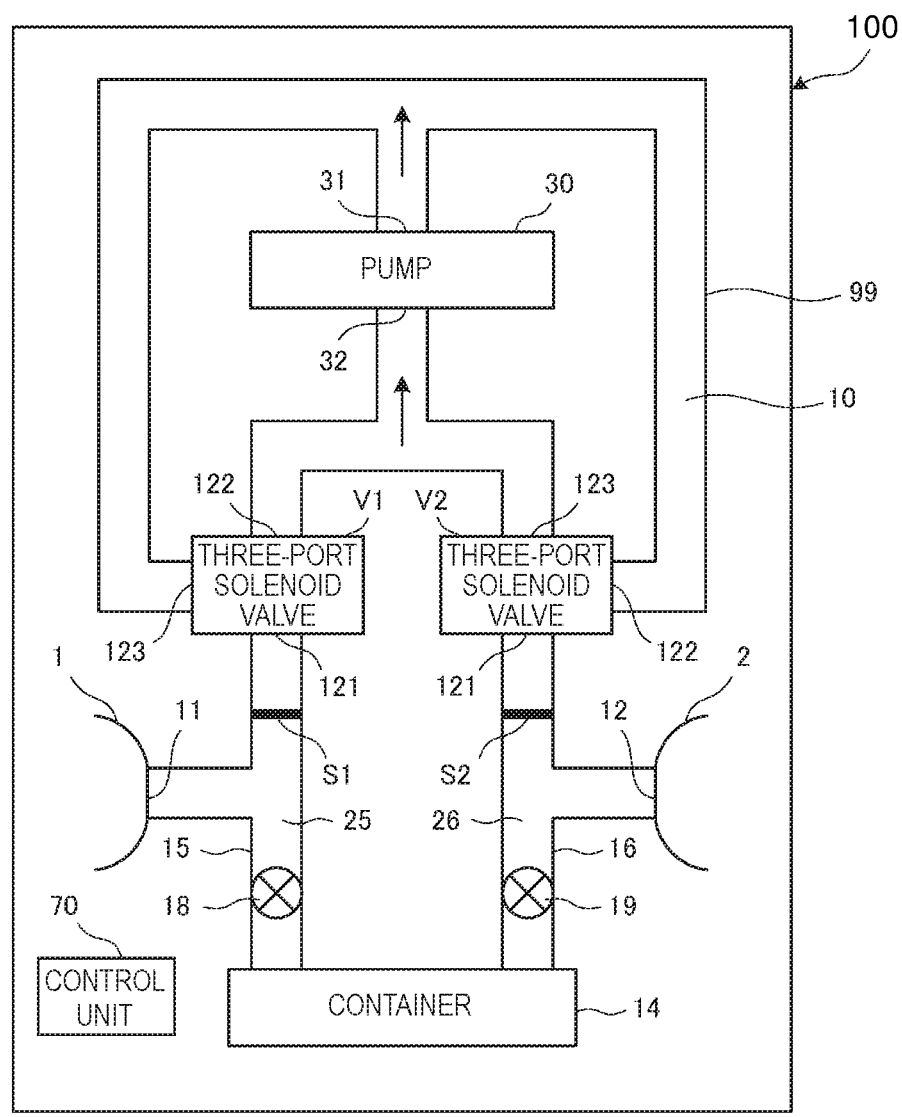
FIG. 4 is an explanatory diagram showing an example of specific configurations of a first switching valve V1 and a second switching valve V2 shown in FIG. 1.
Figure 5:
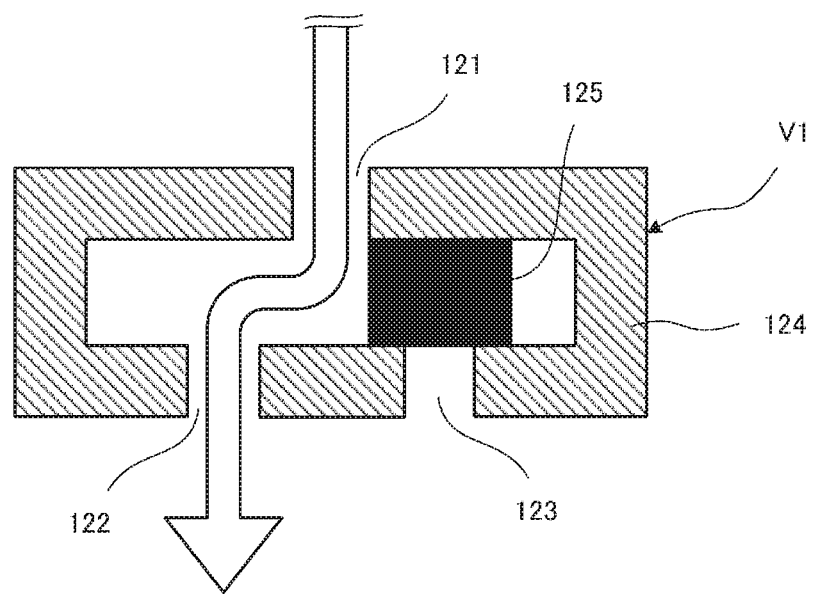
FIG. 5 is a cross-sectional view showing the configuration of the first switching valve V1 shown in FIG. 4.
Figure 6:
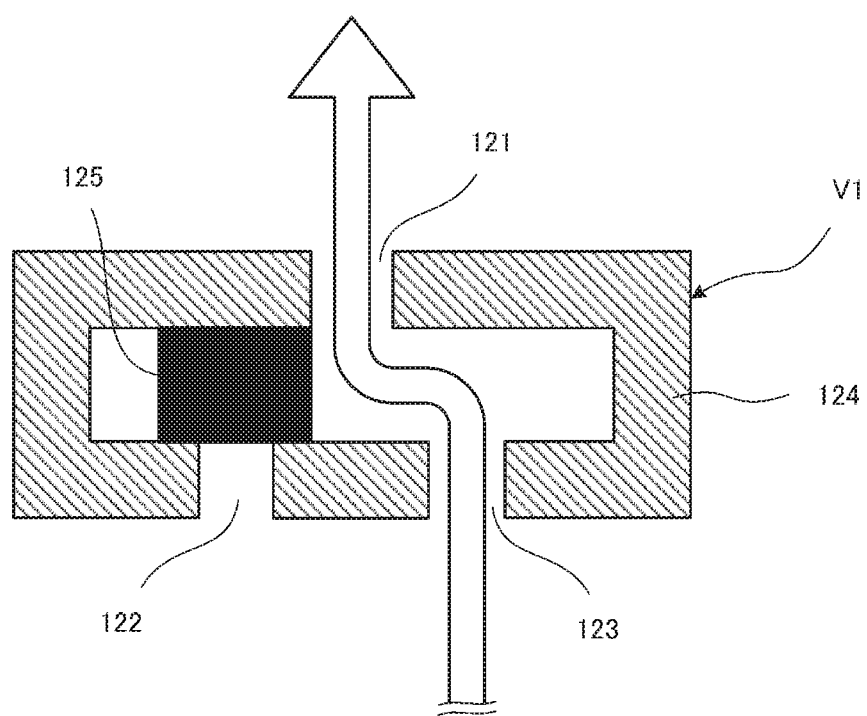
FIG. 6 is a cross-sectional view showing the configuration of the first switching valve V1 shown in FIG. 4.

Hereinafter, an example of specific configurations of the first switching valve V1 and the second switching valve V2 will be described with reference to FIGS. 4 to 6. In FIGS. 4 to 6, the configuration of the first switching valve V1 and the configuration of the second switching valve V2 are the same, and thus the configuration of the first switching valve V1 will be described as a representative of the first switching valve V1 and the second switching valve V2.

FIG. 4 is an explanatory diagram showing an example of the specific configurations of the first switching valve V1 and the second switching valve V2 shown in FIG. 1. FIG. 5 is a cross-sectional view showing the configuration of the first switching valve V1 shown in FIG. 4. FIG. 6 is a cross-sectional view showing the configuration of the first switching valve V1 shown in FIG. 4.

The first switching valve V1 includes: a housing 124 provided with a port 121, a port 122, and a port 123; and a sliding body 125 that slides within the housing 124. The first switching valve V1 is a so-called three-port solenoid valve.

On the basis of an instruction from the control unit 70, the first switching valve V1 causes the sliding body 125 to slide as shown in FIGS. 5 and 6. Accordingly, the first switching valve V1 switches the passage. The second switching valve V2 also switches the passage in the same manner.

As described above, the first switching valve V1 and the second switching valve V2 alternately switch the passage 10 between the first form and the second form as shown in FIGS. 1 and 2.

Here, the first form is a form in which the first separator S1 and the suction hole 32 communicate with each other, the second separator S2 and the discharge hole 31 communicate with each other, and the first separator S1 and the second separator S2 do not communicate with each other.

In addition, the second form is a form in which the first separator S1 and the discharge hole 31 communicate with each other, the second separator S2 and the suction hole 32 communicate with each other, and the first separator S1 and the second separator S2 do not communicate with each other.

Hereinafter, the operation of the breast pump 100 while the pump 30 is operating will be described.

Figure 7:
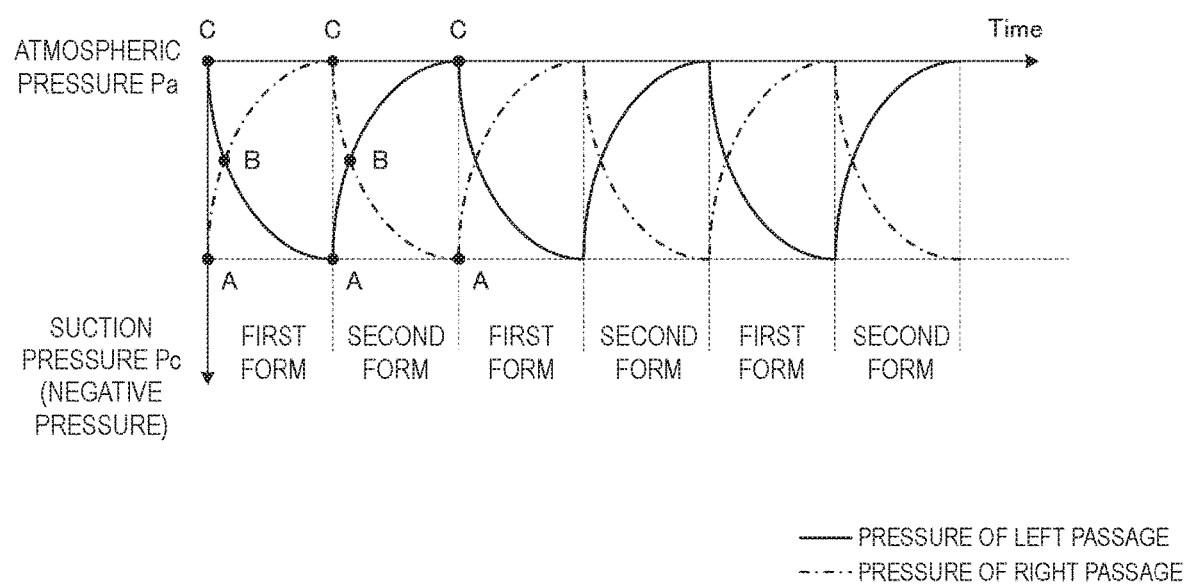
FIG. 7 is a diagram showing the change of the air pressure of a left passage 25 and the change of the air pressure of a right passage 26 while a pump 30 shown in FIGS. 1 and 2 is operating.
Figure 8:
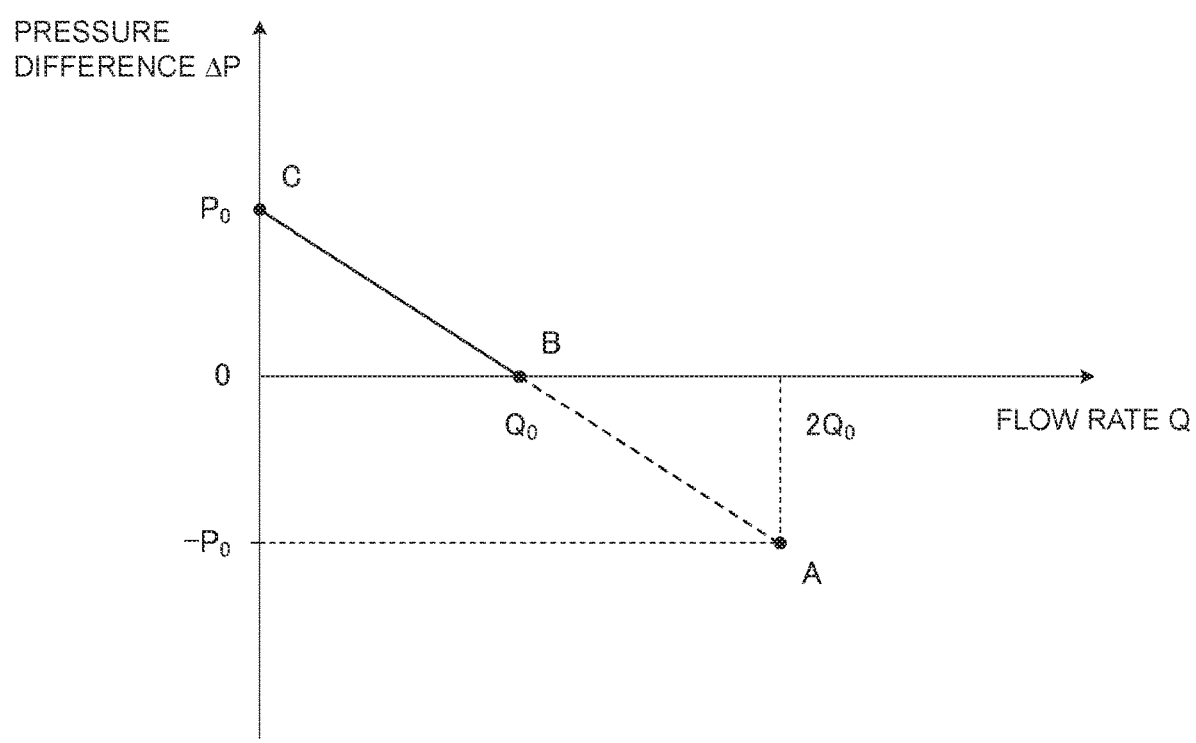
FIG. 8 is a diagram illustrating a relationship between a discharge flow rate and the pressure difference between a discharge hole and a suction hole of the pump.

FIG. 7 is a diagram showing the change of the air pressure of the left passage 25 and the change of the air pressure of the right passage 26 while the pump 30 shown in FIGS. 1 and 2 is operating. FIG. 8 is a diagram illustrating a relationship between a discharge flow rate and the pressure difference between the discharge hole and the suction hole of the pump.

A point A, a point B, and a point C in each form in FIG. 7 correspond to a point A, a point B, and a point C in FIG. 8, respectively.

First, as shown in FIG. 7, the passage 10 is in the first form at a point of time when the pump 30 starts operating. Furthermore, at this point of time, the pressure of the left passage 25 is the atmospheric pressure, and the pressure of the right passage 26 is a negative pressure.

After the pump 30 starts operating, the pump 30 sucks air through the suction hole 32 to elastically deform the first separator S1 such that the first separator S1 projects at the pump 30 side. Accordingly, the volume of the left passage 25 increases. In this manner, the pump 30 generates a negative pressure in the left passage 25 and the closed space 51 as at the point C, the point B, and the point A shown in FIG. 7.

At this time, the check valve 18 restricts backflow, and thus air is not sucked from the container 14 to the left passage 25. Accordingly, the breast milk comes out from the left breast 61. The breast milk coming out from the left breast 61 through the left cup portion 1 is sucked to the left passage 25 and stored in the container 14.

Meanwhile, the pump 30 discharges the air sucked through the suction hole 32, through the discharge hole 31 to elastically deform the second separator S2 such that the second separator S2 projects at the container 14 side. Accordingly, the volume of the right passage 26 decreases. In this manner, the pump 30 increases the pressure of the right passage 26 as at the point A, the point B, and the point C shown in FIG. 7.

When a certain time has elapsed, the control unit 70 instructs the first switching valve V1 and the second switching valve V2 to switch the passage 10 from the first form to the second form.

Next, after the passage 10 is switched to the second form, the pump 30 sucks air through the suction hole 32 to elastically deform the second separator S2 such that the second separator S2 projects at the pump 30 side. Accordingly, the volume of the right passage 26 increases. In this manner, the pump 30 generates a negative pressure in the right passage 26 and the closed space 52 as at the point C, the point B, and the point A shown in FIG. 7.

At this time, the check valve 19 restricts backflow, and thus air is not sucked from the container 14 to the right passage 26. Accordingly, the breast milk comes out from the right breast 62. The breast milk coming out from the right breast 62 through the right cup portion 2 is sucked to the right passage 26 and stored in the container 14.

Meanwhile, the pump 30 discharges the air sucked through the suction hole 32, through the discharge hole 31 to elastically deform the first separator S1 such that the first separator S1 projects at the container 14 side. Accordingly, the volume of the right passage 26 decreases. In this manner, the pump 30 increases the pressure of the left passage 25 as at the point A, the point B, and the point C shown in FIG. 7.

When a certain time has elapsed, the control unit 70 instructs the first switching valve V1 and the second switching valve V2 to switch the passage 10 from the second form to the first form.

Thereafter, while the pump 30 is operating, the control unit 70 alternately switches the passage 10 between the first form and the second form as shown in FIG. 7. Thus, while the pump 30 is operating, the pressure of the left passage 25 and the pressure of the right passage 26 repeat the same change as shown in FIG. 7.

In the operation described above, in the breast pump 100, the pressure of the discharge hole 31 of the pump 30 is negative. Thus, the breast pump 100 is able to achieve a flow rate that is equal to or higher than a no-load flow rate of the pump 30.

As a result, the breast pump 100 is able to shorten time of air exhaust from either one of the left passage 25 or the right passage 26. In addition, at the other of the left passage 25 and the right passage 26, it is possible to use the flow rate of the pump 30, and thus it is possible to open this passage to the atmosphere in a short time.

Hereinafter, the relationship between the pressure and the flow rate of a pump including the pump 30 will be described in detail.

As shown in FIG. 8, where a flow rate when the pressure difference between the discharge hole and the suction hole of the pump is $\Delta P$ is Q, $\Delta P$ and Q satisfy the relationship of $Q/Q0+\Delta P/P0=1$. Therefore, $Q=Q_0(1-\Delta P/P_0)$ is established.

Figure 17:
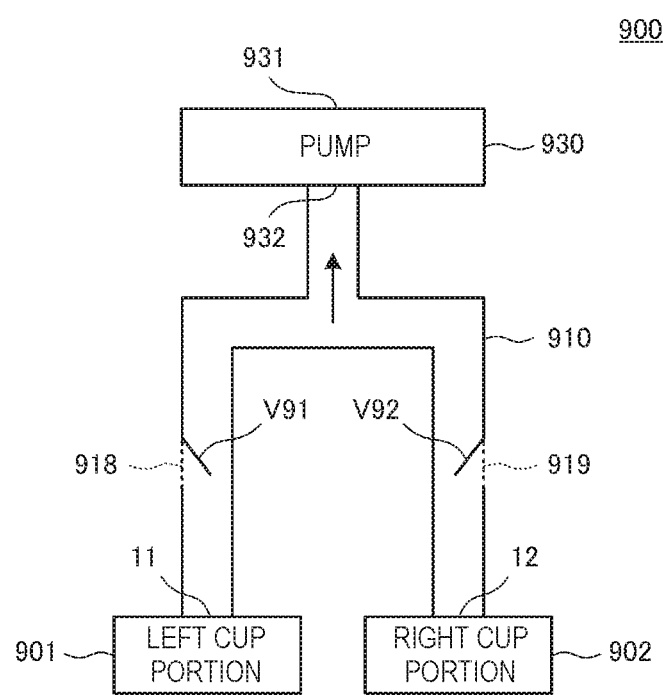
FIG. 17 is an explanatory diagram showing the passage configuration of the breast pump 900 shown in FIG. 16.
Figure 18:
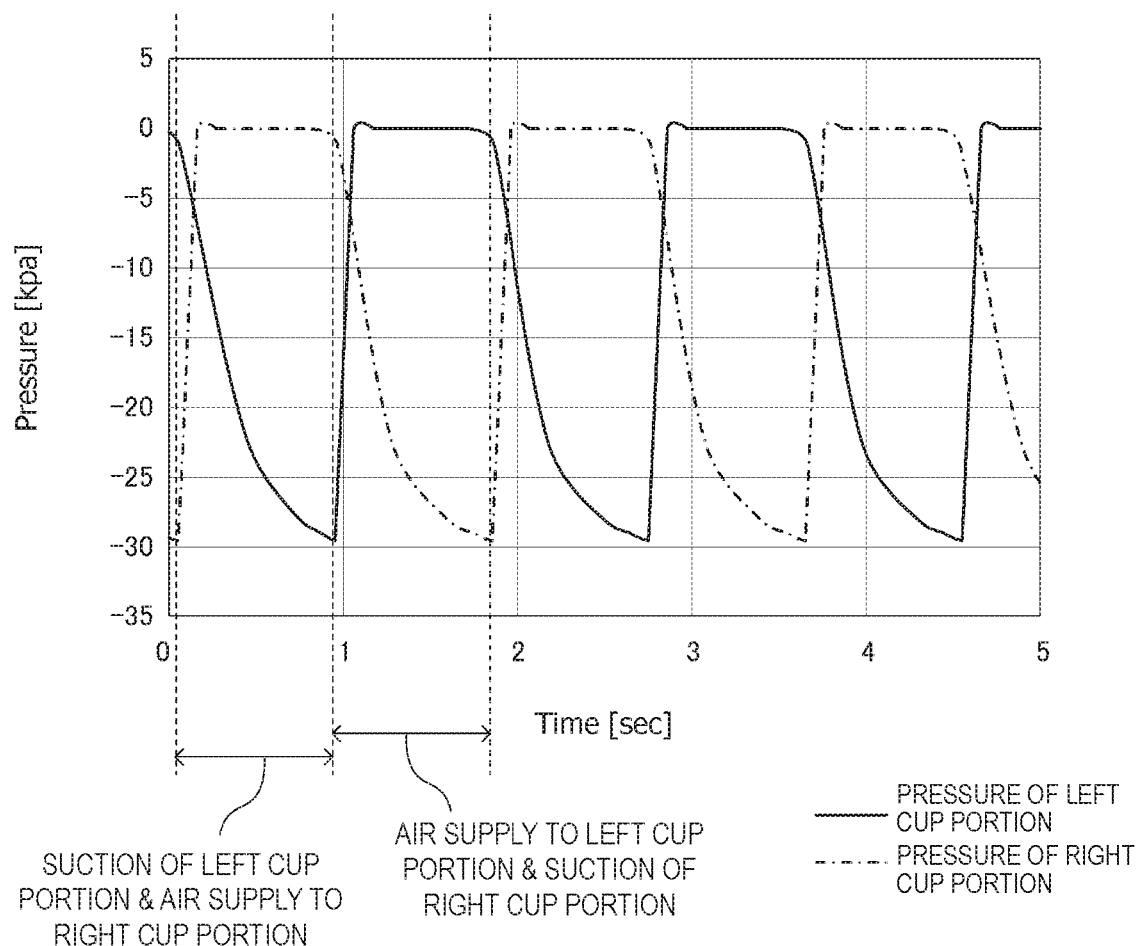
FIG. 18 is a diagram showing the change of the air pressure within a left cup portion 901 and the change of the air pressure within a right cup portion 902 while a pump 930 shown in FIG. 17 is operating.

In the case of the breast pump 900 of Patent Document 1 shown in FIG. 17, the pressure of the discharge hole 931 is always the atmospheric pressure Pa. For example, when the pressure within the left cup portion 901 (=the pressure of the suction hole 932) is Pa−Pc, since the pressure difference $\Delta P=Pc$, $Q=Q_0(1-Pc/P_0)$ is established.

Meanwhile, in the case of the breast pump 100 of the present embodiment, when the pressure of the right cup portion 2 during suction (=the pressure of the suction hole 32) is Pa−Pc, if the breast pump 100 is caused to operate such that the pressure of the left cup portion 1 during air supply (=the pressure of the discharge hole 31) is Pa−(P$_0$−Pc), the pressure difference $\Delta P=2Pc-P_0$ is established, so that $Q=Q_0\{1-(2Pc-P_0)/P_0\}=2Q_0(1-Pc/P_0)$ is established.

That is, the breast pump 100 of the present embodiment is able to achieve a flow rate that is twice that of an existing suction device including the breast pump 900. Therefore, the breast pump 100 of the present embodiment is able to achieve a high suction flow rate with a single small-sized low-cost pump.

In addition, since the pump 30 uses, as a drive source, the piezoelectric element which generates small noise and vibration when operating, it is possible to reduce the noise of the breast pump 100.

Hereinafter, a breast pump 200 according to a second embodiment of the present disclosure will be described.

Figure 9:
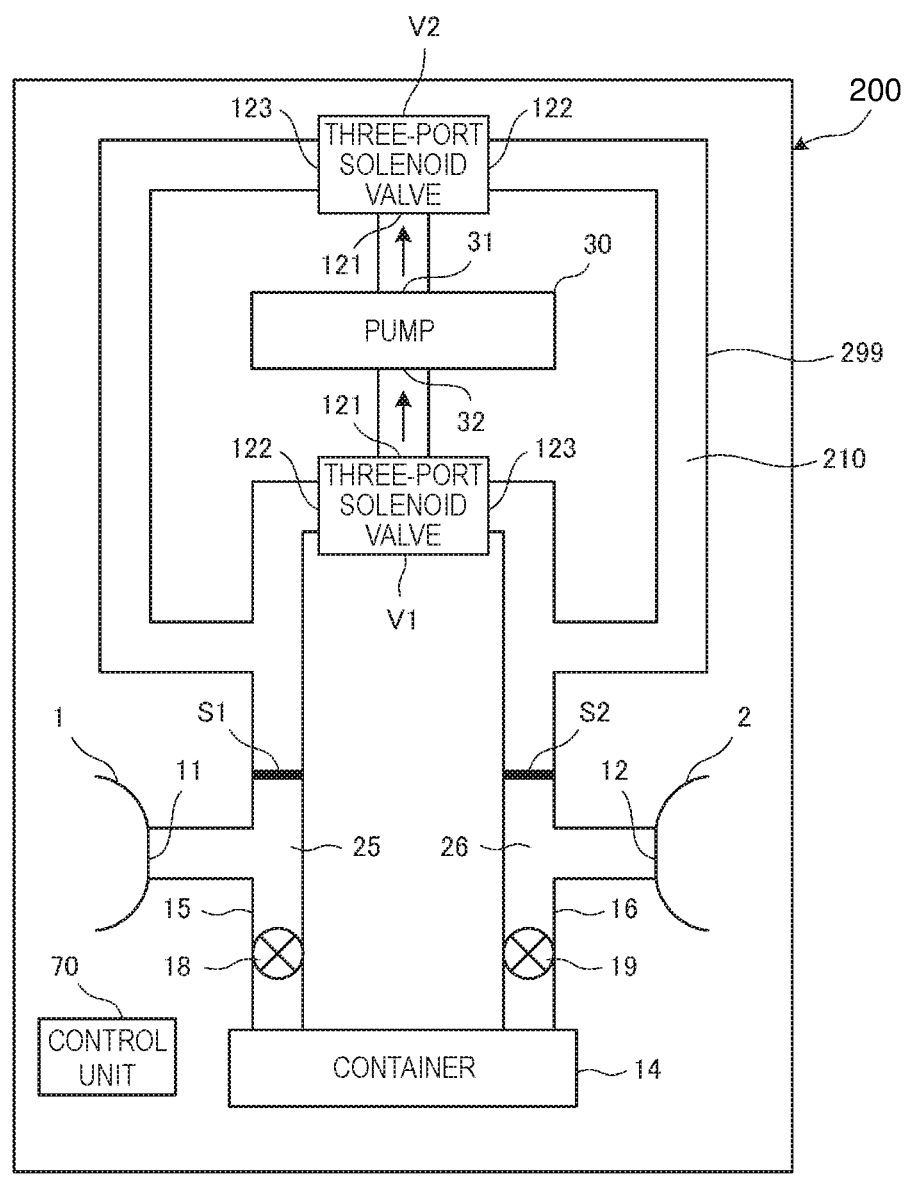
FIG. 9 is a schematic diagram illustrating the configuration of a breast pump 200 according to a second embodiment of the present disclosure.

FIG. 9 is a schematic diagram illustrating the configuration of the breast pump 200 according to the second embodiment of the present disclosure.

The breast pump 200 according to the second embodiment is different from the above-mentioned breast pump 100 in the arrangement of the first switching valve V1 and the second switching valve V2. The other configuration is the same, and thus the description thereof is omitted.

The internal space of a tube 299 forms a passage 210. The passage 210 also connects the first separator S1, which communicates with the closed space 51 via the left passage 25, the second separator S2, which communicates with the closed space 52 via the right passage 26, the discharge hole 31 of the pump 30, and the suction hole 32 of the pump 30.

The first switching valve V1 is provided within the tube 299 that is in the middle of the passage 210. The second switching valve V2 is also provided within the tube 299 that is in the middle of the passage 210.

Therefore, according to the breast pump 200 of the embodiment, the same advantageous effects as those of the breast pump 100 are achieved.

Hereinafter, a breast pump 300 according to a third embodiment of the present disclosure will be described.

Figure 10:
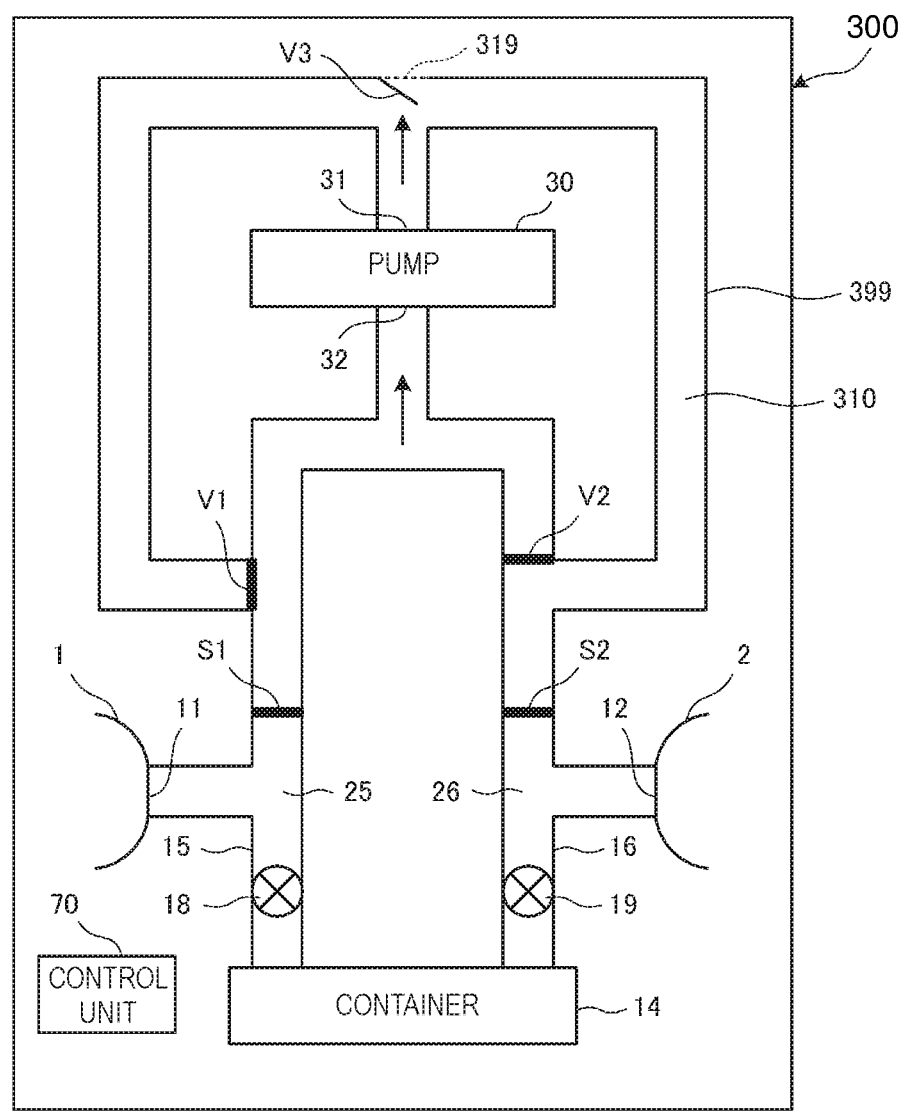
FIG. 10 is a schematic diagram illustrating the configuration of a breast pump 300 according to a third embodiment of the present disclosure.

FIG. 10 is a schematic diagram illustrating the configuration of the breast pump 300 according to the third embodiment of the present disclosure. The breast pump 300 according to the third embodiment is different from the above-mentioned breast pump 100 in an air vent 319 and a vent valve V3. The other configuration is the same, and thus the description thereof is omitted.

The internal space of a tube 399 forms a passage 310. The passage 310 has, between the discharge hole 31 of the pump 30 and the first switching valve V1 and the second switching valve V2, the air vent 319 connected to the outside of the passage 310 and the vent valve V3 for opening/closing the air vent 319.

The first switching valve V1 and the second switching valve V2 switch to an initial form before the pump 30 starts operating. After the pump 30 starts operating, the first switching valve V1 and the second switching valve V2 alternately switch the passage 310 between the first form and the second form.

Here, the initial form is a form in which the vent valve V3 opens (opens to the atmosphere) as shown in FIG. 10, the first separator S1 and the suction hole 32 communicate with each other, the second separator S2 and the discharge hole 31 communicate with each other, and the first separator S1 and the second separator S2 do not communicate with each other.

In addition, the first form is a form in which the vent valve V3 closes, the first separator S1 and the suction hole 32 communicate with each other, the second separator S2 and the discharge hole 31 communicate with each other, and the first separator S1 and the second separator S2 do not communicate with each other.

Moreover, the second form is a form in which the vent valve V3 closes, the first separator S1 and the discharge hole 31 communicate with each other, the second separator S2 and the suction hole 32 communicate with each other, and the first separator S1 and the second separator S2 do not communicate with each other.

Hereinafter, the operation of the breast pump 300 while the pump 30 is operating will be described.

Figure 11:
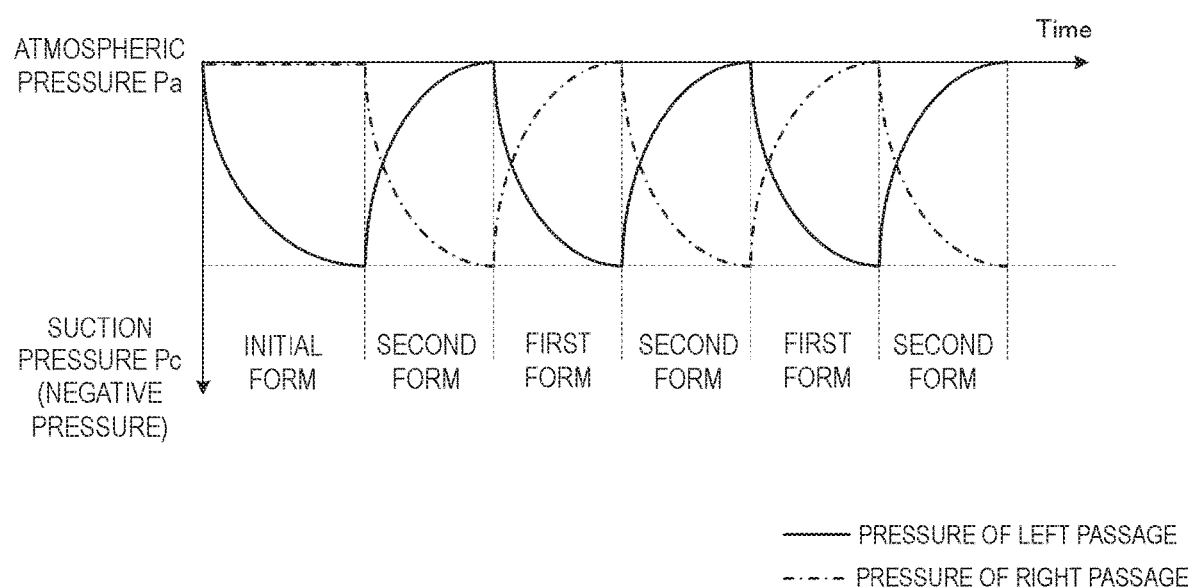
FIG. 11 is a diagram showing the change of the air pressure of a left passage 25 and the change of the air pressure of a right passage 26 while a pump 30 shown in FIG. 10 is operating.

FIG. 11 is a diagram showing the change of the air pressure of the left passage 25 and the change of the air pressure of the right passage 26 while the pump 30 shown in FIG. 10 is operating.

First, at a point of time when the pump 30 starts operating, the passage 310 is in the initial form as shown in FIG. 10. Thus, at this point of time, the pressure of the left passage 25 and the pressure of the right passage 26 are the atmospheric pressure.

After the pump 30 starts operating, the pump 30 sucks air through the suction hole 32 to elastically deform the first separator S1 such that the first separator S1 projects at the pump 30 side. Accordingly, the volume of the left passage 25 increases. In this manner, the pump 30 generates a negative pressure in the closed space 51 and the left passage 25 as shown in FIG. 11.

At this time, the check valve 18 restricts backflow, and thus air is not sucked from the container 14 to the left passage 25. Accordingly, the breast milk comes out from the left breast 61. The breast milk coming out from the left breast 61 through the left cup portion 1 is sucked to the left passage 25 and stored in the container 14.

Meanwhile, the pump 30 discharges the air sucked through the suction hole 32, through the discharge hole 31 and exhausts the air through the air vent 319.

When a certain time has elapsed, the control unit 70 instructs the first switching valve V1, the second switching valve V2, and the vent valve V3 to switch the passage 310 from the initial form to the second form.

Thereafter, while the pump 30 is operating, the control unit 70 alternately switches the passage 310 between the first form and the second form as shown in FIG. 11. Thus, while the pump 30 is operating, the pressure of the left passage 25 and the pressure of the right passage 26 repeats the same change as shown in FIG. 11.

Therefore, according to the breast pump 300 of the embodiment, the same advantageous effects as those of the breast pump 100 are achieved.

In addition, since the air pressure within the passage 310 is caused to be the atmospheric pressure when the breast pump 300 is not used, the load on the tube 399, the left cup portion 1, and the right cup portion 2 is low.

Moreover, since it is possible to detach the left cup portion 1 and the right cup portion 2 after the air pressure within the passage 310 is returned to the atmospheric pressure, the load on the breasts 61 and 62 is low.

Furthermore, by opening/closing the vent valve V3 during the operation, the control of the pressure waveforms of the left passage 25 and the right passage 26 becomes easy.

Hereinafter, a breast pump 400 according to a fourth embodiment of the present disclosure will be described.

Figure 12:
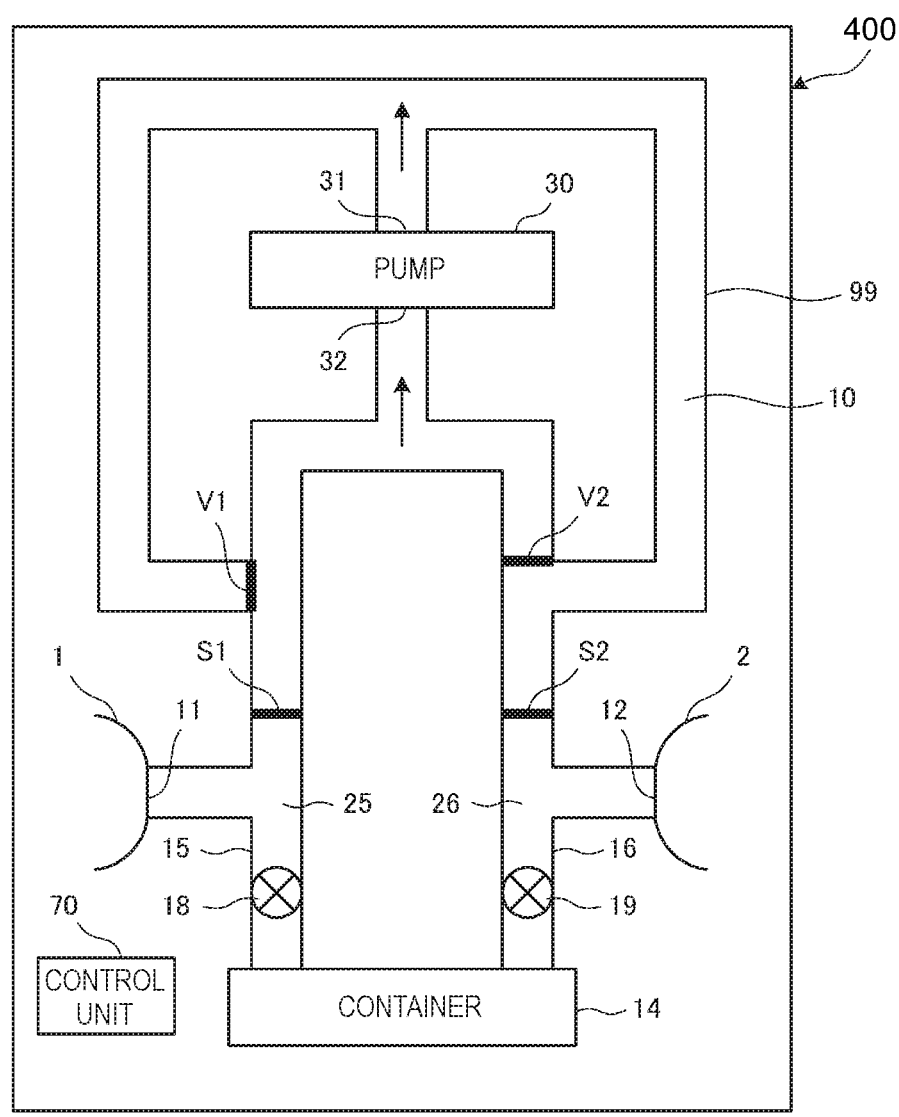
FIG. 12 is an explanatory diagram showing the configuration (first form) of a breast pump 400 according to a fourth embodiment of the present disclosure.
Figure 13:
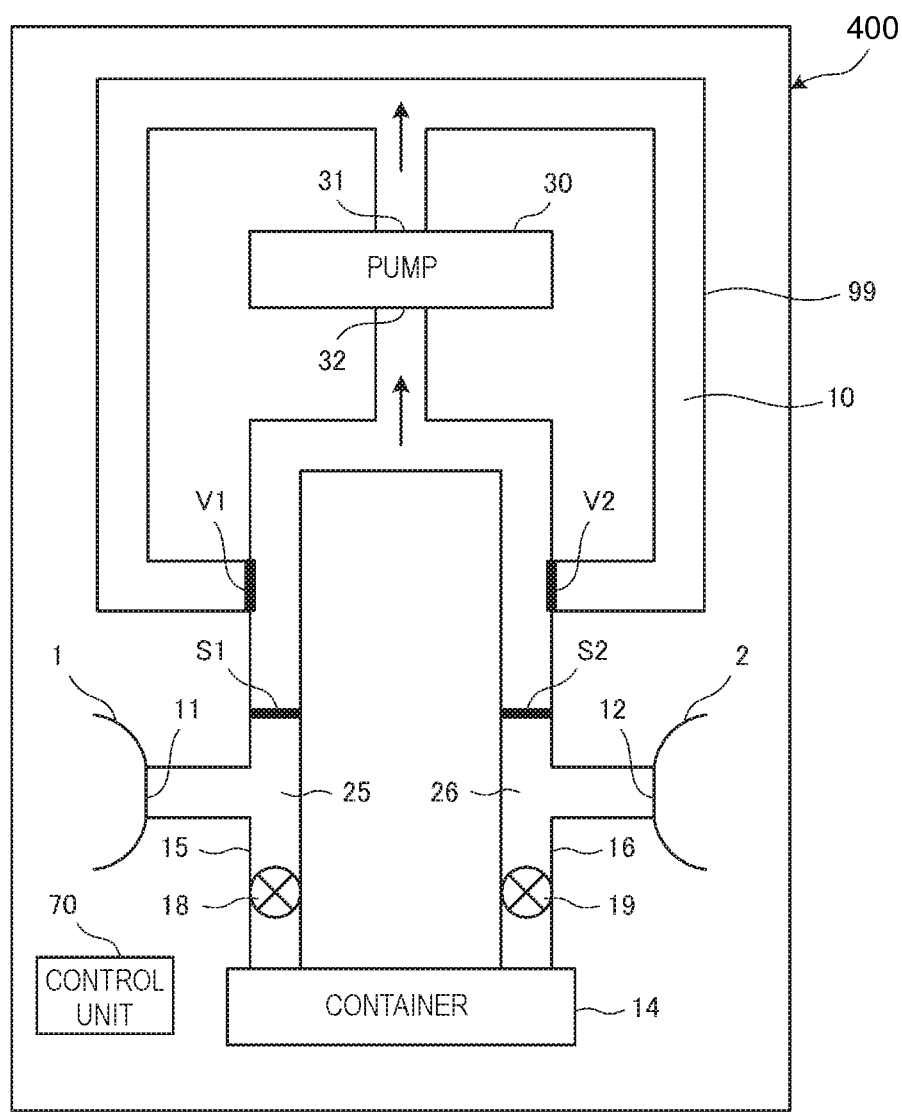
FIG. 13 is an explanatory diagram showing a configuration when a passage 10 is switched to a third form in the breast pump 400 shown in FIG. 12.
Figure 14:
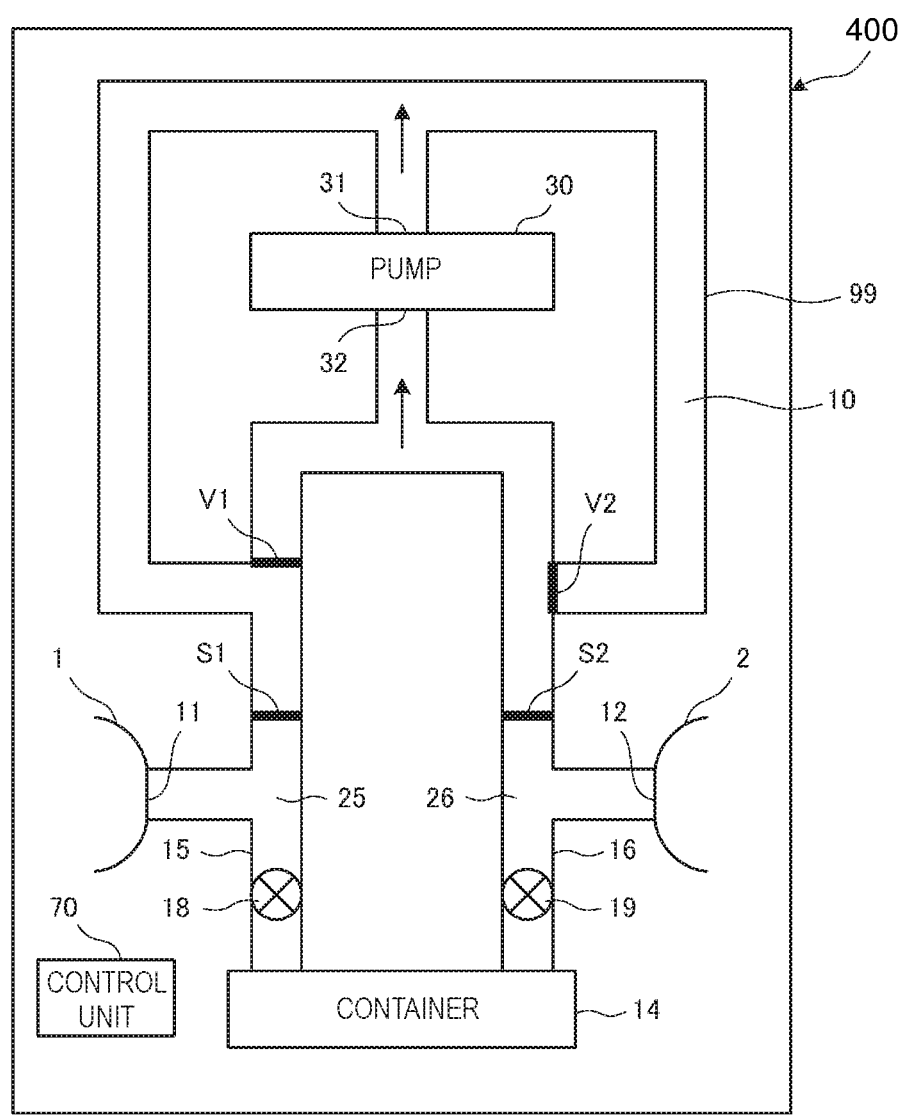
FIG. 14 is an explanatory diagram showing a configuration when the passage 10 is switched to the second form in the breast pump 400 shown in FIG. 12.

FIG. 12 is an explanatory diagram showing the configuration (a first form) of the breast pump 400 according to the fourth embodiment of the present disclosure. FIG. 13 is an explanatory diagram showing a configuration when the passage 10 is switched to a third form in the breast pump 400 shown in FIG. 12. FIG. 14 is an explanatory diagram showing a configuration when the passage 10 is switched to a second form in the breast pump 400 shown in FIG. 12.

The breast pump 400 according to the fourth embodiment is different from the above-mentioned breast pump 100 in operation while the pump 30 is operating. The other configuration is the same, and thus the description thereof is omitted.

Hereinafter, the operation of the breast pump 400 while the pump 30 is operating will be described.

Figure 15:
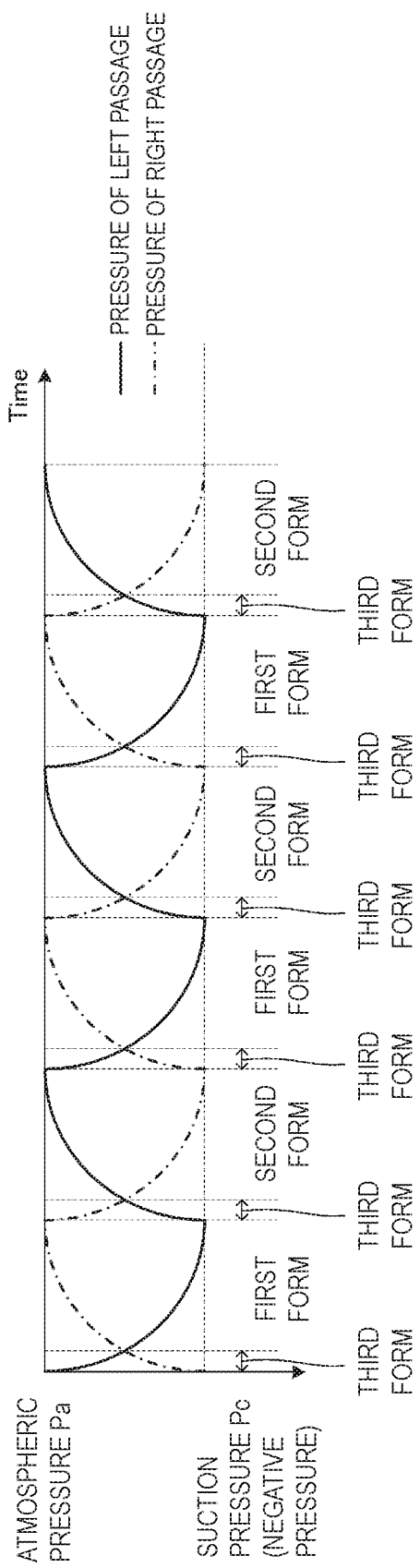
FIG. 15 is a diagram showing the change of the air pressure of a left passage 25 and the change of the air pressure of a right passage 26 while a pump 30 shown in FIGS. 12 to 14 is operating.
Figure 16:
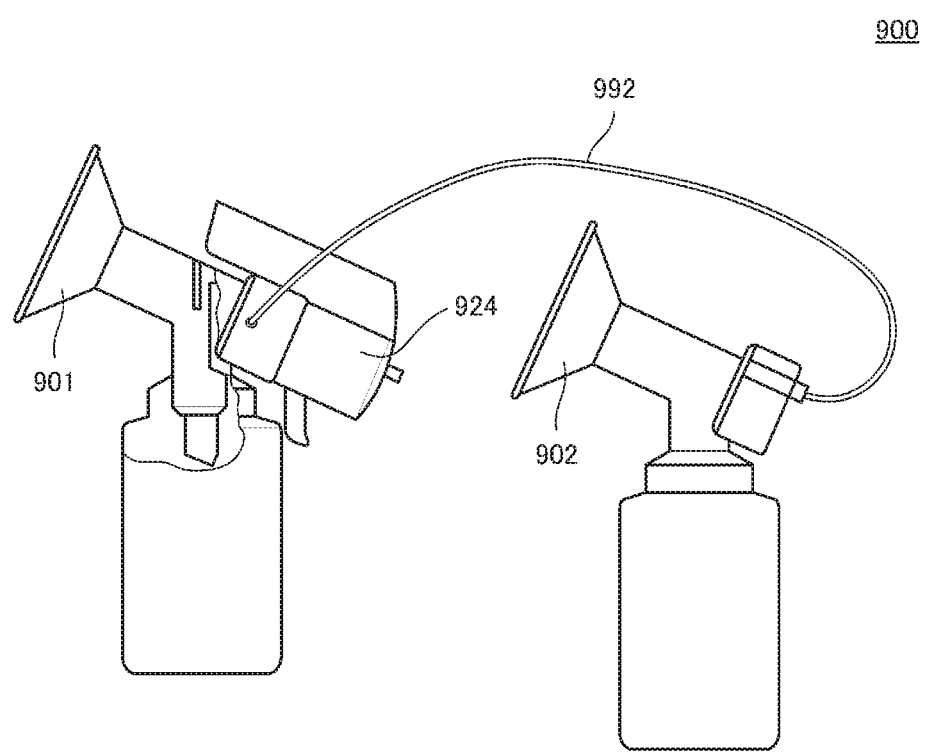
FIG. 16 is an external view showing the configuration of a breast pump 900 according to Patent Document 1.

FIG. 15 is a diagram showing the change of the air pressure of the left passage 25 and the change of the air pressure of the right passage 26 while the pump 30 shown in FIGS. 12 to 14 is operating.

After the pump 30 starts operating, the first switching valve V1 and the second switching valve V2 alternately switch the passage 10 between the first form and the second form. The first switching valve V1 and the second switching valve V2 switch the passage 10 such that the third form is interposed between the first form and the second form.

Here, the first form is a form in which the first separator S1 and the suction hole 32 communicate with each other, the second separator S2 and the discharge hole 31 communicate with each other, and the first separator S1 and the second separator S2 do not communicate with each other.

In addition, the second form is a form in which the first separator S1 and the discharge hole 31 communicate with each other, the second separator S2 and the suction hole 32 communicate with each other, and the first separator S1 and the second separator S2 do not communicate with each other.

Moreover, the third form is a form in which both the first separator S1 and the second separator S2 communicate with the suction hole 32, both the first separator S1 and the second separator S2 do not communicate with the discharge hole 31, and the first separator S1 and the second separator S2 communicate with each other.

Thus, in the breast pump 400, while the pump 30 is operating, the pressure of the left passage 25 and the pressure of the right passage 26 repeat the same change as shown in FIG. 15.

Therefore, according to the breast pump 400 of the embodiment, the same advantageous effects as those of the breast pump 100 are achieved.

Furthermore, since it is possible to stop the operation of the pump 30 during the third form, it is possible to reduce the power consumption.

OTHER EMBODIMENTS

The pump 30 in each of the above-mentioned embodiments includes an actuator that flexurally vibrates by expansion and contraction of the piezoelectric element, but is not limited thereto. For example, the pump 30 may include an actuator that flexurally vibrates by solenoid drive.

In addition, in each of the above embodiments, air is used as the fluid passed through the passage, but the fluid is not limited thereto. In implementation, gas other than air may be used, for example.

Moreover, in each of the above embodiments, the piezoelectrically driven pump 30 is used, but the present disclosure is not limited thereto. In implementation, an electromagnetically driven pump may be used, for example.

Furthermore, in each of the above embodiments, the first worn portion and the second worn portion are worn over the left and right breasts and the breast milk is sucked, but the present disclosure is not limited thereto. In implementation, another liquid (nasal mucus, etc.) may be sucked, for example.

Finally, the description of the above-described embodiments should be considered in all respects as illustrative and not restrictive. The scope of the disclosure is indicated by the appended claims rather than by the above-described embodiments. Furthermore, all changes which come within the meaning and range of equivalency of the claims are intended to be embraced in the scope of the present disclosure.

1 left cup portion
2 right cup portion
10 passage
11 first passage port
12 second passage port
14 container
15 tube
16 tube
18 check valve
19 check valve
24 suction drive unit
25 passage
26 passage
30 pump
31 discharge hole
32 suction hole
51 closed space
52 closed space
61 left breast
62 right breast
70 control unit
99 tube
100 breast pump
121 port
122 port
123 port
124 housing
125 sliding body
200 breast pump
210 passage
299 tube
300 breast pump
310 passage
319 air vent
399 tube
400 breast pump
900 breast pump
901 left cup portion
902 right cup portion
910 passage
918 hole
919 hole
930 pump
931 discharge hole
932 suction hole
992 tube
S1 first separator
S2 second separator
V1 first switching valve
V2 second switching valve
V3 vent valve
V91 switching valve
V92 switching valve

The invention claimed is:

1. A suction device comprising:
a pump having a discharge hole and a suction hole;
a first worn portion having a first connection portion;
a second worn portion having a second connection portion;
a passage connecting the first connection portion, the second connection portion, the discharge hole, and the suction hole; and
a switching mechanism provided in a middle of the passage and configured to switch the passage, wherein the switching mechanism switches the passage between:
a first form in which the first connection portion and the suction hole communicate with each other, the second connection portion and the discharge hole communicate with each other, and the first connection portion and the second connection portion do not communicate with each other;
a second form in which the first connection portion and the discharge hole communicate with each other, the second connection portion and the suction hole communicate with each other, and the first connection portion and the second connection portion do not communicate with each other; and
a third form in which the first connection portion and the second connection portion communicate with each other, both the first connection portion and the second connection portion communicate with the suction hole, and both the first connection portion and the second connection portion do not communicate with the discharge hole.

2. The suction device according to claim 1, wherein the switching mechanism alternately switches the passage between the first form, the second form and the third form.

3. The suction device according to claim 2, wherein the passage has, between the discharge hole and the switching mechanism in the passage, an air vent connected to an outside of the passage and a vent valve configured to open/close the air vent.

4. The suction device according to claim 2, wherein the switching mechanism includes a valve.

5. The suction device according to claim 2, wherein the pump includes a piezoelectric element and is operated by the piezoelectric element.

6. The suction device according to claim 1, wherein the passage has, between the discharge hole and the switching mechanism in the passage, an air vent connected to an outside of the passage and a vent valve configured to open/close the air vent.

7. The suction device according to claim 6, wherein the switching mechanism includes a valve.

8. The suction device according to claim 6, wherein the pump includes a piezoelectric element and is operated by the piezoelectric element.

9. The suction device according to claim 1, wherein the switching mechanism includes a valve.

10. The suction device according to claim 9, wherein the valve is a solenoid valve.

11. The suction device according to claim 10, wherein the solenoid valve is a three-port solenoid valve.

12. The suction device according to claim 11, wherein the pump includes a piezoelectric element and is operated by the piezoelectric element.

13. The suction device according to claim 10, wherein the pump includes a piezoelectric element and is operated by the piezoelectric element.

14. The suction device according to claim 9, wherein the pump includes a piezoelectric element and is operated by the piezoelectric element.

15. The suction device according to claim 1, wherein the pump includes a piezoelectric element and is operated by the piezoelectric element.

\* \* \* \* \*